United States Patent
Nakajima et al.

(10) Patent No.: US 9,044,358 B2
(45) Date of Patent: Jun. 2, 2015

(54) ABSORBENT ARTICLE WITH WAIST-CUFF

(75) Inventors: Kaiyo Nakajima, Kagawa (JP);
Toshimitsu Baba, Kagawa (JP)

(73) Assignee: UNICHARM CORPORATION, Ehime (JP)

( * ) Notice: Subject to any disclaimer, the term of this patent is extended or adjusted under 35 U.S.C. 154(b) by 671 days.

(21) Appl. No.: 13/260,407

(22) PCT Filed: Mar. 25, 2010

(86) PCT No.: PCT/JP2010/002099
§ 371 (c)(1),
(2), (4) Date: Sep. 26, 2011

(87) PCT Pub. No.: WO2010/109866
PCT Pub. Date: Sep. 30, 2010

(65) Prior Publication Data
US 2012/0022482 A1      Jan. 26, 2012

(30) Foreign Application Priority Data

Mar. 25, 2009   (JP) ................................ 2009-075198

(51) Int. Cl.
*A61F 13/15*   (2006.01)
*A61F 13/20*   (2006.01)
*A61F 13/494*   (2006.01)

(52) U.S. Cl.
CPC ................................ *A61F 13/49466* (2013.01)

(58) Field of Classification Search
CPC ................... A61F 13/49011; A61F 13/49466; A61F 13/49473; A61F 13/49019; A61F 13/4902; A61F 13/49061; A61F 13/494; A61F 13/49413; A61F 13/49446; B32B 37/0076

USPC ........... 604/385.01, 385.03, 385.101, 385.24, 604/385.27–385.31, 386–387
See application file for complete search history.

(56) References Cited

U.S. PATENT DOCUMENTS 4,857,067 A * 8/1989 Wood et al. .................... 604/389
5,188,626 A * 2/1993 Toyoda et al. ............ 604/385.27
(Continued)

FOREIGN PATENT DOCUMENTS

EP      1192922 A1    4/2002
EP      1199058 A1    4/2002
(Continued)

OTHER PUBLICATIONS

European Search Report issued in corresponding Application No. 10755668.0, dated Feb. 4, 2013.
(Continued)

*Primary Examiner* — Michele M Kidwell
(74) *Attorney, Agent, or Firm* — Lowe Hauptman & Ham, LLP

(57) ABSTRACT

An absorbent article is provided with a waist-cuff to prevent body waste from leaking beyond a waist-opening. An elastic sheet is used for the waist-cuff to be held in contact with the wearer's skin even if the wearer moves. The waist-cuff and a chassis may be joined to each other so as to be separated from each other in the vicinity of an absorbent structure to assure that fitness of the waist-cuff to the wearer's skin is not significantly affected by movement of the wearer and, at the same time, to assure that leg-cuffs can rise without being collapsed by the waist-cuff. The ends of the leg-cuffs are interleaved between the waist-cuff and the chassis to prevent body waste from leaking through a clearance which would otherwise be defined between the leg-cuffs and the waist-cuff.

18 Claims, 6 Drawing Sheets

(56) References Cited

U.S. PATENT DOCUMENTS

| | | | | |
|---|---|---|---|---|
| 5,464,401 A | * | 11/1995 | Hasse et al. | 604/385.25 |
| 5,868,725 A | * | 2/1999 | Coles et al. | 604/385.23 |
| 6,280,426 B1 | * | 8/2001 | Turner et al. | 604/385.01 |
| 6,383,170 B1 | | 5/2002 | Mishima et al. | |
| 6,506,185 B1 | * | 1/2003 | Sauer et al. | 604/385.01 |
| 6,706,030 B1 | | 3/2004 | Okuda et al. | |
| 2002/0151860 A1 | * | 10/2002 | Klemp et al. | 604/385.19 |
| 2002/0165517 A1 | * | 11/2002 | Datta et al. | 604/385.22 |
| 2006/0270302 A1 | * | 11/2006 | Ando et al. | 442/328 |

FOREIGN PATENT DOCUMENTS

| | | |
|---|---|---|
| JP | 08-150163 A | 6/1996 |
| JP | 10-179633 A | 7/1998 |
| JP | 11-099168 A | 4/1999 |
| JP | 2000-254171 A | 9/2000 |
| JP | 2000-325394 A | 11/2000 |
| JP | 2001-252303 A | 9/2001 |
| JP | 3315993 B2 | 6/2002 |
| JP | 2003-010237 A | 1/2003 |
| JP | 2003010237 A | 1/2003 |
| JP | 2008-284288 A | 11/2008 |
| JP | 4215370 B2 | 11/2008 |

OTHER PUBLICATIONS

International Search Report for PCT/JP2010/002099 mailed Jul. 13, 2010.

* cited by examiner

FIG.1
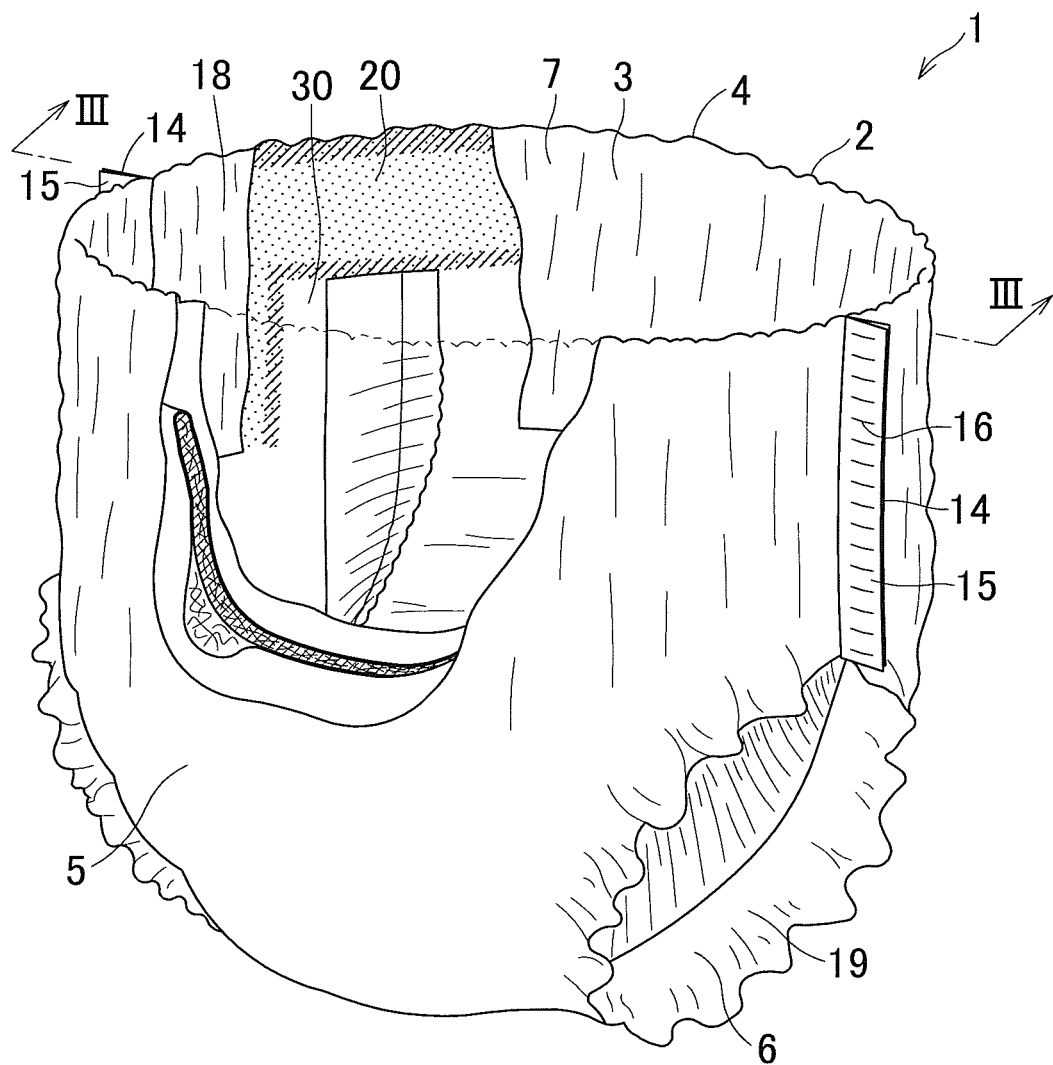
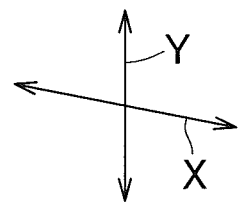

ABSORBENT ARTICLE WITH WAIST-CUFF

RELATED APPLICATIONS

The present application is a National Phase of International Application Number PCT/JP2010/002099, filed Mar. 25, 2010 and claims priority from, Japanese Application Number 2009-075198, filed Mar. 25, 2009.

TECHNICAL FIELD

The present disclosure relates to absorbent articles such as disposable diapers, toilet-training pants or incontinent briefs.

BACKGROUND

JP 3315993 B2 discloses a pant-type diaper comprising a liquid-pervious inner sheet, a liquid-impervious outer sheet and an absorbent structure sandwiched between these sheets. The diaper includes a front waist region adapted to lie on the wearer's ventral side and a rear waist region adapted to lie on the wearer's dorsal side. Transversely opposite side edges of the front waist region are joined to the associated side edges of the rear waist region so as to define a waist-opening and a pair of leg-openings. This diaper includes waist elastic members attached along a periphery of the waist-opening, and a waist-cuff extending, on the side of the diaper facing the wearer's skin, from the waist-opening toward the crotch region.

In this diaper, the waist-cuff is provided with an elastic member so that the waist-cuff may be put in close contact upon contraction of the elastic member so as to define a pocket between this waist-cuff and the diaper chassis and thereby to prevent body waste from leaking beyond the waist-opening.

In this diaper, the waist-cuff is left free from the diaper chassis except along the periphery of the waist-opening and at the transversely opposite ends of the front and rear waist regions. As a consequence, the pocket is apt to be deformed or even to be collapsed as the wearer's body moves, causing the body waste having been captured by the pocket to leak out from the diaper.

JP 4215370 B2 discloses a further diaper in which the waist-cuff is fixed to the diaper chassis in the vicinity of transversely opposite side edges of an absorbent structure. In this diaper, therefore, the shape retention of the pocket is correspondingly improved so that the pocket is not easily collapsed.

JP 4215370 B2 further discloses a diaper provided with leg cuffs formed along the transversely opposite side edges of the absorbent structure.

When the absorbent structure absorbs or receives body waste, the absorbent structure is drawn downward under a weight of body waste absorbed or received by the absorbent structure. Therefore, the waist-cuff might be drawn apart from the wearer's skin under a weight of body waste absorbed or received by the absorbent structure when the waist-cuff is fixed to the chassis in the vicinity of the absorbent structure.

When the diaper has a pair of leg-cuffs, the waist-cuff might partially overlap the leg-cuffs. In such diaper, if the waist-cuff is fixed in the vicinity of the side edges of the absorbent structure, the leg-cuffs may be collapsed to cause a leaking of body waste. Alternatively, the waist-cuffs might not overlap the leg-cuffs. In such diaper, there might be regions without both leg-cuffs and waist-cuff where leakage of body waste might occur.

CITATION LIST

Patent Literature

[PTL 1]
Japanese Patent Publication No. 3315993 B2
[PTL 2]
Japanese Patent Publication No. 4215370 B2

SUMMARY

One or more embodiments of the invention relates to an absorbent article, comprising: a chassis, an absorbent structure, and a waist-cuff. The chassis has longitudinal and transverse directions orthogonal to each other, a skin-contact surface, a first waist region, a second waist region, and a crotch region extending in the longitudinal direction between the first waist region and the second waist region. A waist-opening is defined by cooperation of the first and second waist regions. A pair of leg-openings is defined by cooperation of the first and second waist regions and the crotch region. The waist-cuff is attached to the skin-contact surface in a region adjacent to the waist-opening in the first waist region or in the first and second waist regions.

In this article, the waist-cuff is at least partially elastic and is left free from the chassis in a middle region overlapping the absorbent structure and in non-joined regions outboard of and in region adjacent transversely opposite lateral edges of the absorbent structure.

BRIEF DESCRIPTION OF DRAWINGS

[FIG. 1]
FIG. 1 is a partially cutaway perspective view of a diaper according to one embodiment of the present invention.
FIG. 2 is a partially cutaway plan view of the diaper of FIG. 1 in a flatly developed state.
FIG. 3 is a sectional view taken along the line III-III in FIG. 1.
FIG. 4 is a partial view of a partially cutaway plan view of similar to FIG. 2 showing another embodiment.
FIG. 5 is a partial view similar to FIG. 4 showing another embodiment.
FIG. 6 is a view similar to FIG. 2 showing another embodiment.

DETAILED DESCRIPTION

Figure 2:
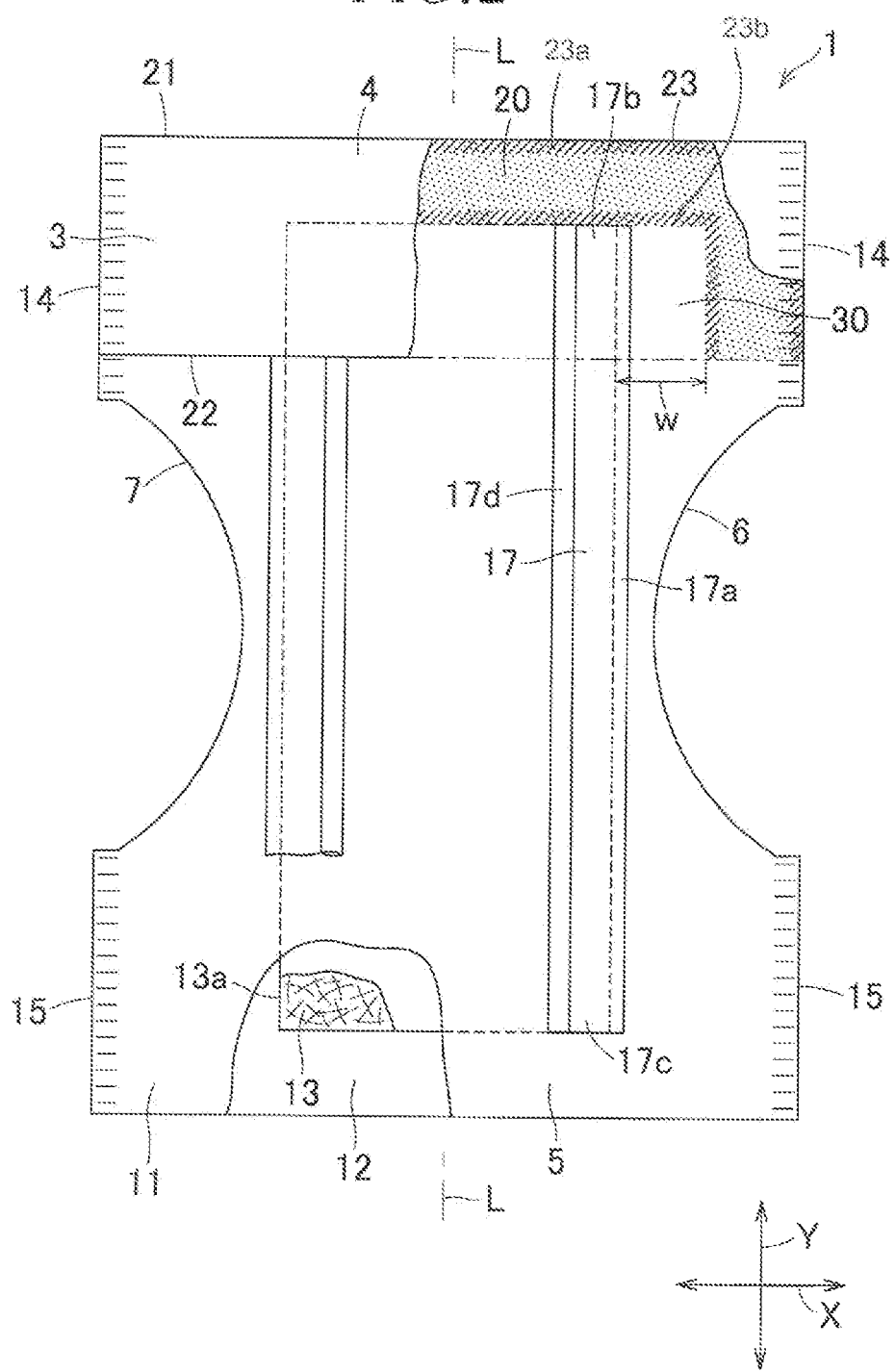
[FIG. 2]

Details of absorbent articles according to exemplary embodiments of the present invention will be more fully understood from the following description given hereunder in reference to the accompanying drawings.

FIG. 1 is a partially cutaway perspective view of a diaper 1 according to an exemplary embodiment of the present invention.

As shown in FIG. 1, the diaper 1 includes a chassis 2 and a waist-cuff 3. FIG. 1 shows the chassis 2 as well as the waist-cuff 3 as being partially cutaway.

The chassis 2 comprises a front waist region 4 referred to also as a first waist region herein, a rear waist region 5 referred to also as a second waist region herein and a crotch region 6 extending between these front and rear waist regions 4, 5. A direction extending from the front waist region 4 across the crotch region 6 into the rear waist region 5 is referred to as a longitudinal direction Y, and a direction orthogonally intersecting with this longitudinal direction Y is referred to as a transverse direction X.

With the diaper 1 being put on the wearer's body, the front waist region 4 lies on the wearer's ventral side and the rear waist region 5 lies on the wearer's dorsal side. The chassis 2 has a skin-contact surface 7 coming in contact with the wearer's skin when the diaper 1 is put on the wearer's body.

The front waist region 4 has a pair of lateral edges 14 opposed to each other in the transverse direction X, and the rear waist region 5 also has a pair of lateral edges 15 opposed to each other in the transverse direction X. The lateral edges 14 of the front waist region 4 and the lateral edges 15 of the rear waist region 5 are put flat and bonded together over the skin-contact surface so as to form a plurality of side seams 16. The front and rear waist regions 4, 5 cooperate with each other to define a waist-opening 18, and the front and rear waist regions 4, 5 cooperate with the crotch region 6 to define a pair of leg-openings 19.

The waist-cuff 3 is disposed on the skin-contact surface 7 of the front waist region 4 of the chassis 2 generally over the entire region of the front waist region 4 between the opposite lateral edges 14. In some embodiments, lateral edges of the waist-cuff 3 are sandwiched between, and bonded at side seams 16, to the lateral edges 14, 15 of the front and rear waist regions 4, 5, respectively.

FIG. 2 is a plan view showing the diaper 1 of FIG. 1 in the flatly developed state after the lateral edges 14, 14 and 15, 15 have been disconnected one from another. Referring to FIG. 2, the chassis 2 as well as the waist-cuff 3 is shown as being partially cutaway. FIG. 2 shows all elastic members of the diaper in a stretched state.

Figure 3:
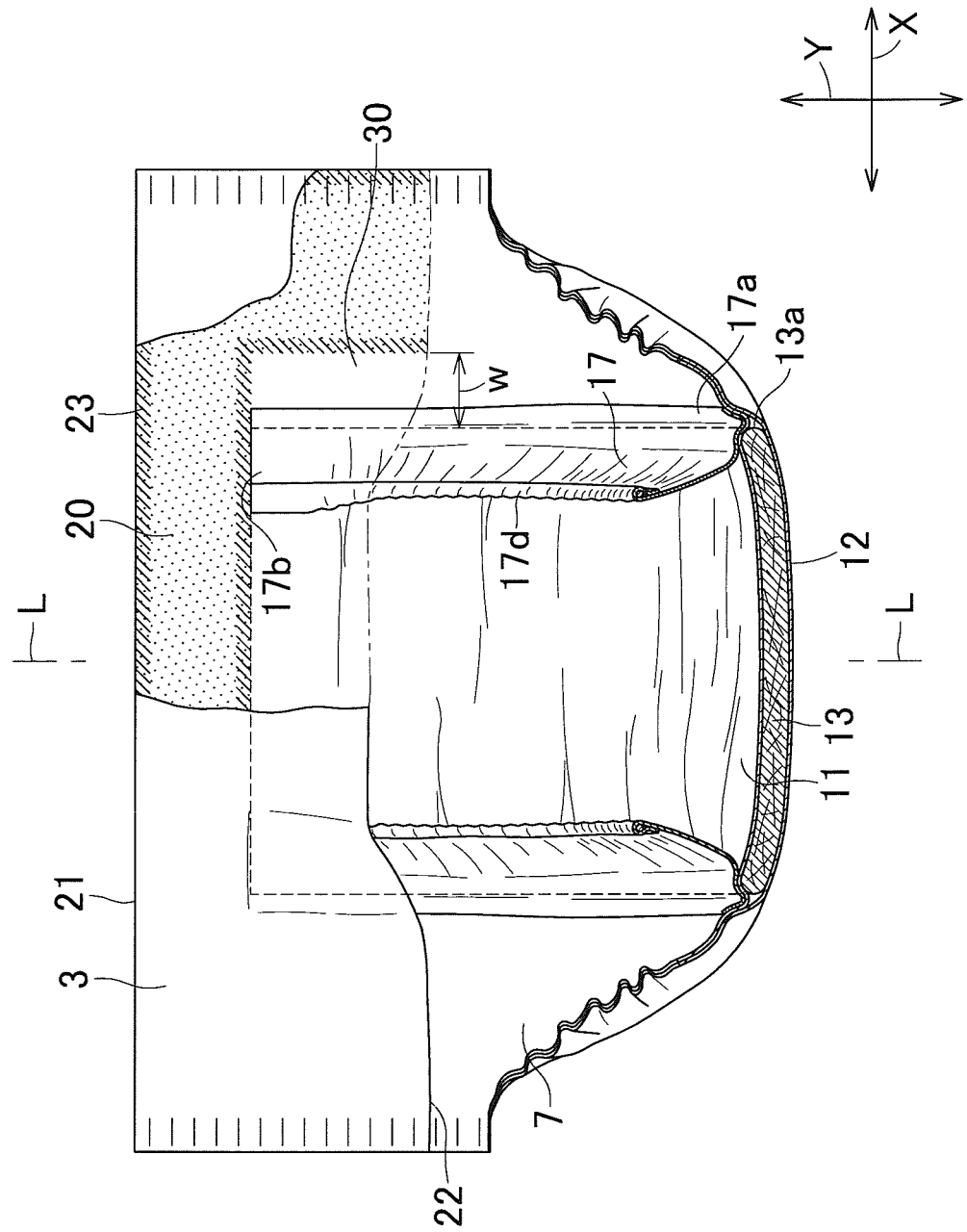
[FIG. 3]

FIG. 3 is a sectional view taken along the line III-III in FIG. 1. In FIG. 3, the waist-cuff is shown as being partially cutaway.

As will be appreciated from FIGS. 2 and 3, the diaper 1 is shaped so as to be symmetric about the longitudinal center line L bisecting a dimension of the diaper 1 in the transverse direction X. The chassis 2 comprises an inner sheet 11 defining the skin-contact surface 7, an outer sheet 12 defining the surface opposed to the skin-contact surface 7, and an absorbent structure 13 sandwiched between these inner and outer sheets 11, 12.

The waist-cuff 3 is formed of an elastic sheet having a predetermined width extending from its waist-side end 21 on the waist-opening 18 to its crotch-side end 22 toward the crotch region 6, and bonded to the skin-contact surface 7 of the chassis 2 in a joined region 20 indicated by a dot-pattern. The joined region 20 is defined by regions lying along the waist-side end 21 and the lateral edges 14. In the joined region 20, the waist-cuff 3 is not only joined to the chassis 2 but also reinforced with the chassis 2. In other words, the joined region 20 serves also as the reinforced region. It should be appreciated here that the waist-cuff 3 is not directly bonded to the chassis 2 in a pair of rectangular non-joined regions 30 extending outward beyond the transversely opposite lateral edges of the absorbent structure 13 by a dimension (width) w, respectively, corresponding to the width of the non-joined region. In other words, non-joined regions 30 are located outboard of the transversely opposite lateral edges of the absorbent structure 13 and are free of direct attachment to (or left free from) the chassis 2. With this unique arrangement, as will be apparent from FIG. 3, the waist-cuff 3 can be spaced from the skin-contact surface 7 of the chassis 2 in the middle region overlapping the absorbent structure 13 and in of the regions adjacent to the lateral edges 13a of the absorbent structure 13 opposed in the transverse direction X.

As shown by FIG. 2, a pair of leg-cuffs 17 is attached to the skin-contact surface 7 of the chassis 2 along the lateral edges 13a of the absorbent structure 13. Each of the leg-cuffs 17 has a fixed edge 17a extending along the associated lateral edge 13a of the absorbent structure 13, a free edge 17d, and front and rear ends 17b, 17c. The front and rear ends 17b, 17c, referred to also as first and second ends herein and which lie in the front and rear waist regions 4, 5, respectively. These front and rear ends 17b, 17c overlap the front and rear ends of the absorbent structure 13, respectively. The free edges 17d of the leg-cuffs 17 are located inboard of the fixed edges 17a.

The leg-cuff 17 is bonded to the skin-contact surface 7 of the chassis 2 along the fixed edge 17a and at the front and rear ends 17b, 17c (see FIG. 2), and an elastic member is attached in a stretched state to the free edge 17d so as to be contractible in the longitudinal direction Y (see FIG. 3).

When the diaper 1 shown by FIGS. 1 through 3 is put on the wearer's body, the waist-cuff 3 closely fits to the ventral region of the wearer. In the non-joined region 30, the waist-cuff 3 cooperates with the skin-contact surface 7 of the chassis 2 to form a pocket serving to prevent body waste from leaking beyond the waist-opening 18. The leg-cuffs 17 are spaced upward from the skin-contact surface 7 under contraction of the elastic members so as to fit to the wearer's skin along the respective free edges 17d. At the same time, the leg-cuffs 17 separate the crotch region 6 of the chassis 2 from the wearer's skin.

Such arrangement allows the waist-cuff 3 to be spaced, due to elastic contraction of (i) the waist-cuff 3 and/or (ii) the free edges 17d of the leg-cuffs 17 from the skin-contact surface 7 of the chassis 2 in the vicinity of the absorbent structure 13 as viewed in the transverse direction. Thus, even if the chassis 2 is pulled downward under increased weight of the absorbent structure 13 which has absorbed or received body waste, the waist-cuff 3 would not follow movement of the absorbent structure 13 to be spaced from the wearer's skin. This arrangement ensures also that the leg-cuffs 17 are reliably raised by the respective elastic members between the waist-cuff 3 and the chassis 2 without being collapsed. In this way, no clearance is left between the waist-cuff 3 or the leg-cuffs 17 and the wearer's skin, and thereby body waste is reliably received by the diaper without leaking.

The transverse dimension w by which the non-joined region 30 extending outward beyond the lateral edges of the absorbent structure 13 on the crotch-side end 22 of the waist-cuff 3 is ranging, in some embodiments, from about 10 mm to 30 mm.

Figure 4:
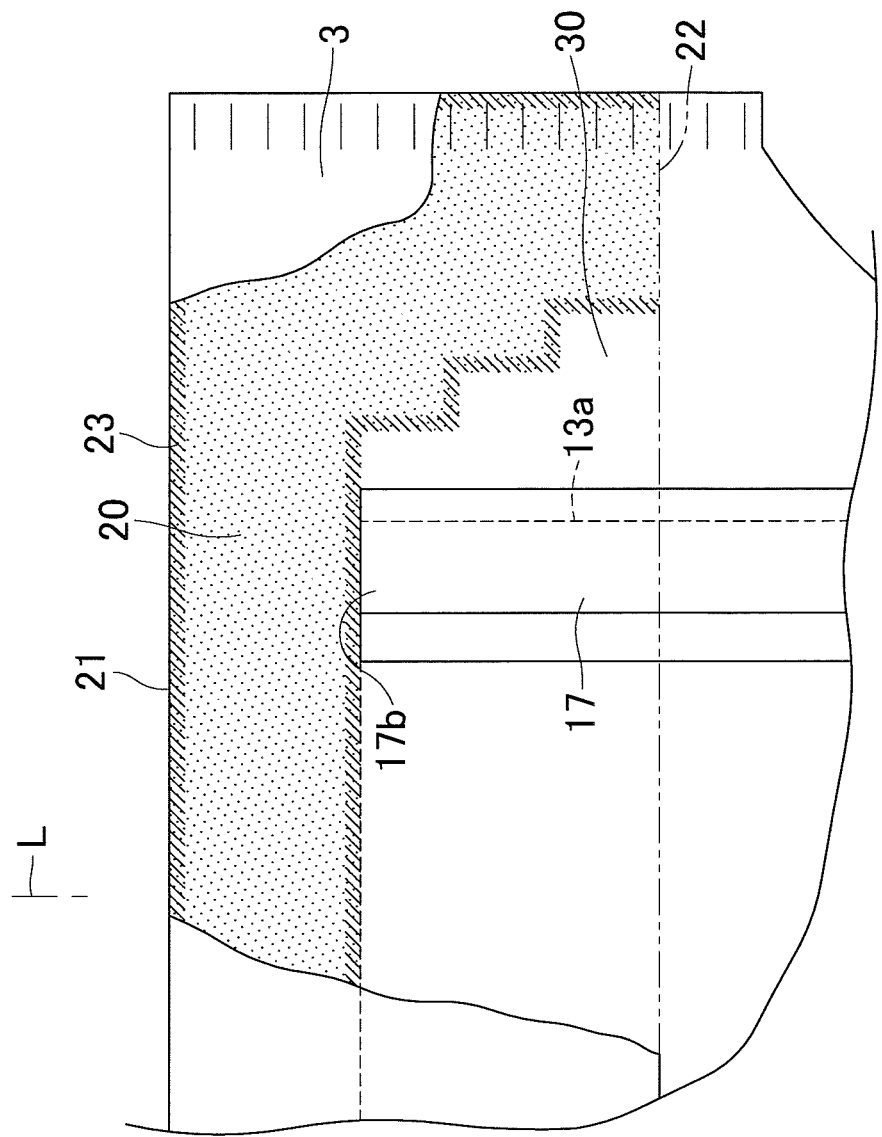
[FIG. 4]

FIG. 4 is a view similar to FIG. 2, showing an alternative exemplary embodiment of the diaper 1 in which the joined region 20 and the non-joined region 30 have different shapes from those in the diaper 1 of FIG. 2.

According to this exemplary embodiment, the non-joined region 30 is shaped to have its width increasing in a stepwise fashion in a direction towards the crotch-side end 22 in the longitudinal direction.

Figure 5:
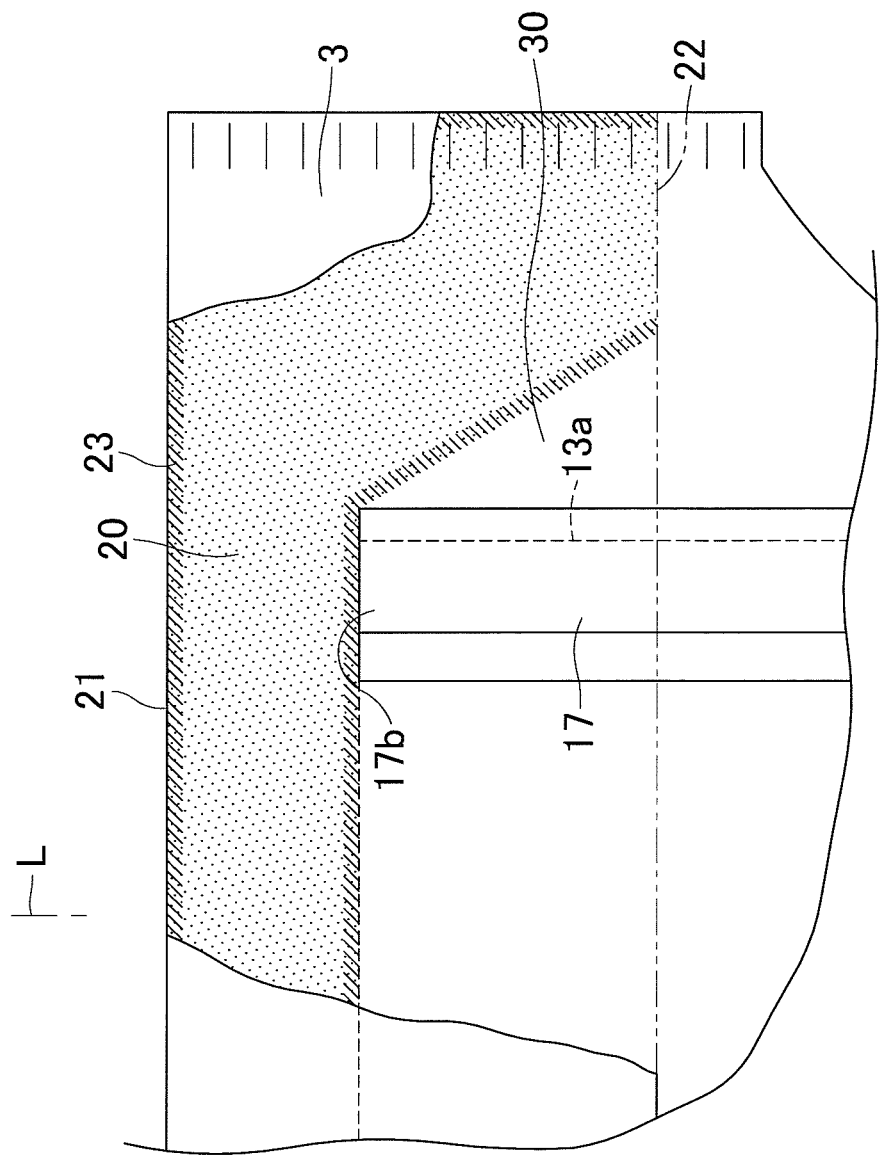
[FIG. 5]

When the diaper 1 is put on the wearer's body, a height of the leg-cuffs 17 by which these leg-cuffs 17 are spaced upward from the skin-contact surface 7 is gradually increased from the front end 17b toward the crotch region 6. Likewise, a height of the waist-cuff 3 by which the waist-cuff 3 is spaced upward from the skin-contact surface 7 is also gradually increased from the front end 17b toward the crotch region 6 (see FIG. 3). In the diaper 1 shown by FIG. 4, the waist-cuff 3 is bonded to the skin-contact surface 7 in a manner such that the region of the waist-cuff 3 adapted to be spaced upward from the skin-contact surface 7 is enlarged toward the crotch-side end 22 in a stepwise fashion. As a result, the shapes of the waist-cuff 3 and the leg-cuffs 17 can be further stabilized when the diaper is being worn. While FIG. 4 shows a particular embodiment in which the width of the non-joined region 30 is increased in three steps, the number of the steps may be two or more than three. The non-joined region 30 may have its width increased toward the crotch-side end 22 of the waist-cuff 3 in a continuous fashion (i.e., gradually) rather than in a stepwise fashion. In other words, the non-joined region 30 may have a trapezoidal shape, as shown in FIG. 5. In some embodiments, the width of the non-joined region 30 is largest at the crotch-side end 22 of the waist-cuff 3, and is in the range of about 10 mm to 30 mm.

The joined region 20 as shown by FIGS. 2 through 4 is not essential to be joined wholly to the skin-contact surface 7. In some embodiments, the joined region 20 is joined to the skin-contact surface 7 at least in edge bonding regions 23 that extend along transversely opposite side edges 14, in the region adjacent to the waist-side end 21 and in the region adjacent to the non-joined region 30, as shown in FIG. 2 with stripes. A remainder of the joined region 20 outside the edge bonding regions 23 may be joined to the skin-contact surface 7 or left free of direct bonding to the skin-contact surface 7. The edge bonding regions include a first edge bonding region 23a extending in transversely opposite side edges of the waist-cuff 3 and in the waist-side end 21 of the waist-cuff 3, and a second edge bonding region 23b inward of the first edge bonding region 23a in the longitudinal direction L and in the transverse direction X. The second edge bonding region 23b extends along the non-joined regions 30 and about an end of the sbsorbent structure 13.

While the waist-cuff 3 is entirely formed of elastic sheet in the diaper 1 shown by FIGS. 1 through 4, it is possible to combine an elastic sheet with an inelastic sheet to form the waist-cuff 3. For example, the joined region 20 adapted to be joined to the skin-contact surface 7 of the chassis 2 may partially be formed of an inelastic sheet. When an inelastic sheet is used in the region adjacent to the crotch-side end 22, such inelastic sheet is used, in some embodiments, only in a region of 5 mm or less from the crotch-side end 22.

It is possible to form the leg-cuff 17 wholly using an elastic sheet.

While the front and rear ends 17b, 17c of the leg-cuffs 17 overlap with the front and rear ends, respectively, of the absorbent structure 13 in the diaper 1 according to the embodiments described above, it is possible, without departing from the scope of the invention, to place these front and rear ends 17b, 17c to one side of the front and rear ends of the absorbent structure 13 either toward the crotch region 6 or toward the waist-opening 18. In some embodiments, the non-joined region 30 of the waist-cuff 3 extends in the longitudinal direction Y along a region of the leg-cuff 17, in which the free edge 17d is contractible, by a distance of 10 mm or more. The 10 mm or more distance is measured when the elastic member of the leg-cuff 17 is in the stretched state as shown in FIG. 2 or 4.

According to another embodiment of the invention, the diaper 1 is provided also in the second waist region with another waist-cuff similar to the waist-cuff 3 in the first waist region. In a further embodiment, the waist-cuff 3 is provided in the second waist region only.

Figure 6:
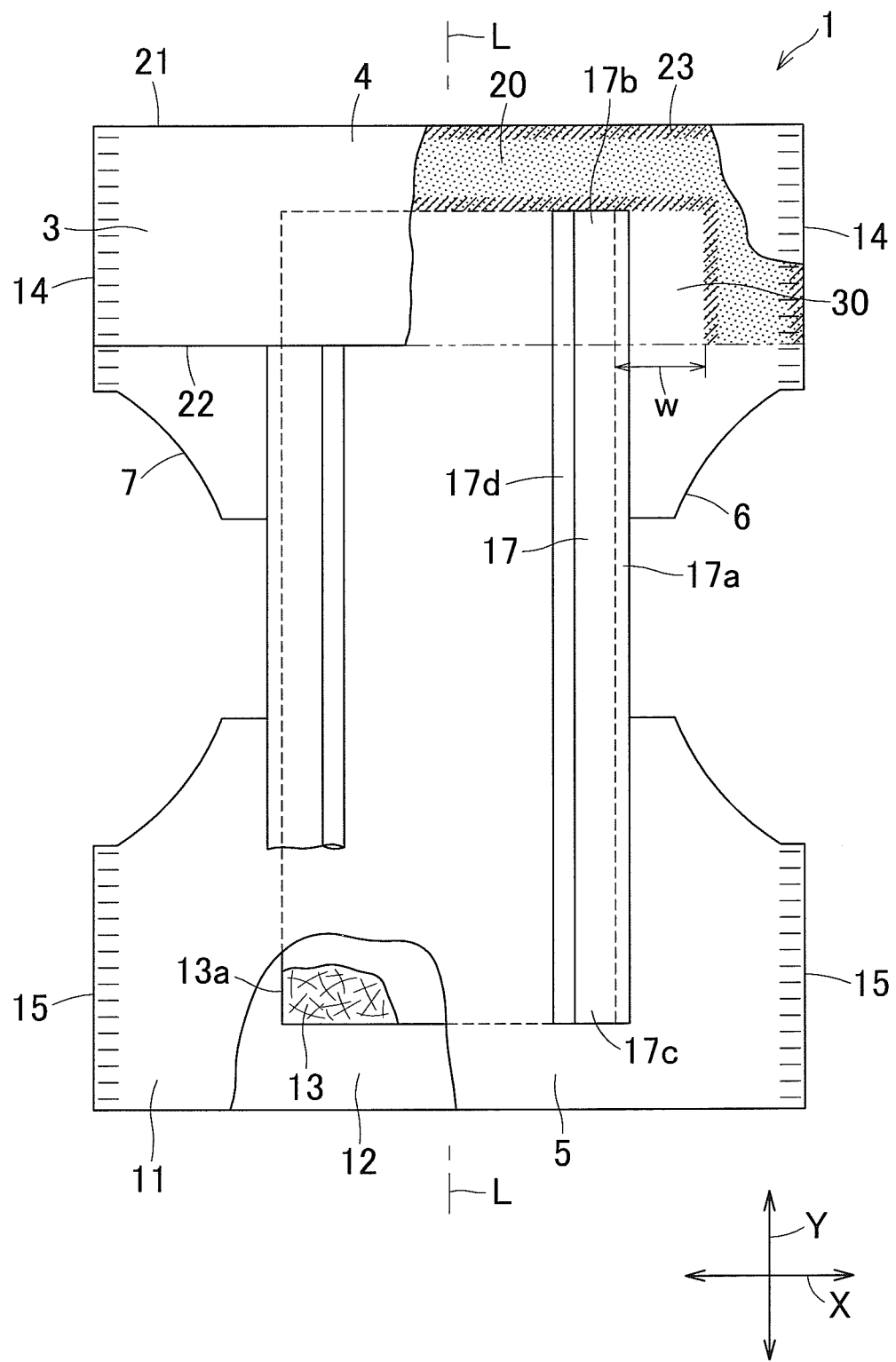
[FIG. 6]

While the chassis 2 in the diaper 1 illustrated by FIGS. 1 through 4 comprises the liquid-pervious inner sheet 11 extending over the entire skin-contact surface 7, the liquid-impervious outer sheet 12 extending over the entire surface opposite to the skin-contact surface 7, and the absorbent structure 13 sandwiched between these inner and outer sheets 11, 12, the present invention is not limited to such embodiments. For example, further embodiments of the present invention may be implemented in the form of a diaper having a chassis comprising the inner and outer sheets forming a basic chassis, and the absorbent structure wrapped with a liquid-pervious sheet and fixed to the inner sheet of this basic chassis that is adapted to face the wearer's skin. It is also possible to implement yet further embodiments of the invention in the form of a diaper shown in FIG. 6 having a chassis comprising two independent waist members respectively adapted to define the first waist region and the second waist region, a crotch member defining the crotch region and made of a liquid-impervious sheet, and an absorbent structure wrapped with a liquid-pervious sheet and fixed to the side of the crotch member that is adapted to face the wearer's skin. The absorbent structure may be wrapped with the liquid-pervious sheet only on the side that is adapted to face the wearer's skin, or on both sides of the absorbent structure.

Sheet material used to form the waist-cuff or the leg-cuffs is, in some embodiments, liquid-impervious.

While the elastic sheet used for the above embodiments may include elastic plastic film or the like, the most preferable material is an elastic fibrous non-woven fabric. In some embodiments, the leg elastic members are formed of (1) an elastically stretchable non-woven fabric made of elastic fibers, such as urethane elastic fibers, or (2) an elastically stretchable non-woven fabric made of elastically stretchable fibers mixed with non-elastically stretchable thermoplastic synthetic fibers. In other embodiments, a plurality of rubber strings can be used as the leg elastic members.

As stock materials used to implement one or more embodiments of the present invention, those commonly used for relevant articles, such as disposable diapers and menstruation napkins may be used. For example, a fibrous non-woven fabric or a perforated plastic film as the liquid-pervious sheet; a moisture-pervious but liquid-impervious plastic film or a laminate of a moisture-pervious but liquid-impervious plastic film and a fibrous non-woven fabric as the liquid-impervious sheet; a mixture of fluff pulp and super-absorbent polymer particles and optionally thermoplastic staple fibers wrapped with a liquid-absorbent and dispersant sheet, such as tissue paper, as the absorbent structure; and a natural or synthetic rubber or an elastic fibrous non-woven fabric as the elastic members.

According to one or more embodiments of the present invention, the diaper components maybe joined together by means usually used in the relevant technical field, for example, bonding by adhesive such as hot melt adhesive and sealing such as heat sealing or ultrasonic sealing particularly for thermoplastic sheets.

While the absorbent articles according to embodiments of the present invention have been exemplarily described to be pants-type disposable diapers, further embodiments of the present invention may be implemented also in the form of so-called open-type diapers provided on the lateral edges with releasably fastening means, such as mechanical or adhesive fasteners, instead of the seams of the pants-type diapers.

The aspect(s) of the present invention described above may be arranged in at least the following items:

(i) The absorbent article (1) comprises a chassis (2) having longitudinal and transverse directions (Y, X) orthogonal to each other, a skin-contact surface (7), a first waist region (4), a second waist region (5), a crotch region (6) extending in the longitudinal direction between the first waist region and the second waist region, an absorbent structure (13), a waist-opening (18) defined by cooperation of the first and second waist regions, a pair of leg-openings (19) being defined by cooperation of the first and second waist regions and the crotch region, and a waist-cuff (3) attached to the skin-contact surface along in a region adjacent to the waist-opening in at least the first waist region of the first and second waist regions, the waist-cuff being at least partially elastic; and the waist-cuff is left free from the chassis in a middle region overlapping the absorbent structure and in non-joined regions (30) outboard of and in regions adjacent to transversely opposite lateral edges (13a) of the absorbent structure.

The aspect(s) of the present invention described in the above item (i) may provide one ore more of the following advantageous effects:

(a) The waist-cuff is wholly or partially elastic and is joined to the chassis so as to be spaced from the chassis in the vicinity of the absorbent structure. With such arrangement, the waist-cuff can be kept in close contact with the wearer's skin even when the wearer moves or even when the weight of the absorbent structure is increased because of absorbed or received body waste.

Additionally, one or more of the following embodiments are provided in accordance with further aspects:

(ii) The absorbent article further comprises a pair of leg-cuffs (17) attached to the skin-contact surface of the chassis, each of the leg-cuffs having a fixed edge (17a) attached to an associated one of the lateral edges of the absorbent structure, a free edge (17d) being elastically contractible in the longitudinal direction and first and second ends (17b, 17c) respectively lying in the first and second waist regions, and the first end or the first and second ends is sandwiched between the chassis and the waist-cuff.

(iii) The chassis comprises an inner sheet (11) lying on a skin-contact side, an outer sheet (12) opposed to the inner sheet and the absorbent structure is sandwiched between the inner and outer sheets.

(iv) The chassis comprises an inner sheet (11) lying on a skin-contact side, an outer sheet (12) opposed to the inner sheet and the absorbent structure is provided on the inner sheet.

(v) The chassis comprises elongated waist members defining the first and second waist regions, respectively, a crotch member defining the crotch region and the absorbent structure is provided on a skin-contact side of the crotch member.

(vi) The waist-cuff is formed of an elastic fibrous nonwoven fabric.

(vii) The first and second waist regions are joined along lateral edges thereof to define the waist-opening and the pair of leg-openings, with lateral edges (14, 15) of the waist-cuff being sandwiched between and bonded to the lateral edges of the first and second waist regions.

(viii) The waist-cuff is adapted to be spaced from the skin-contact surface toward a wearer's body under at least elastic contraction of the waist-cuff.

(ix) The waist-cuff is spaced from the skin-contact surface toward the wearer's body under elastic contraction of the waist-cuff and the free edge of each of the leg-cuffs.

(x) The free edges of the leg-cuffs are located inboard of the fixed edges of the leg-cuffs.

(xi) A width of each of the non-joined regions of the waist-cuff in the vicinities of the transversely opposite lateral edges of the absorbent structure is increased toward the crotch region.

(xii) A width of each of the non-joined regions of the waist-cuff in the vicinities of the transversely opposite lateral edges of the absorbent structure is increased in a stepwise fashion toward the crotch region.

(xiii) A width of each of the regions of the waist-cuff in the vicinities of the transversely opposite lateral edges of the absorbent structure is gradually increased toward the crotch region.

(xiv) A width (w) of each of the non-joined regions of the waist-cuff in the vicinities of the transversely opposite lateral edges of the absorbent structure is in a range of 10 to 30 mm.

(xv) The waist-cuff is directly wholly joined to the skin-contact surface except in the non-joined regions.

(xvi) The waist-cuff is directly joined to the skin-contact surface at least along transversely opposite side edges of the first waist region, in a vicinity of a crotch-side end (22) of the waist-cuff, and in a vicinity of the non-joined regions.

(xvii) The waist-cuff comprises an elastic sheet and an inelastic sheet, wherein the inelastic sheet is provided only in a region of 5 mm or less from a crotch-side end of the waist-cuff.

(xviii) Each of the non-joined regions of the waist-cuff extends in the longitudinal direction along a region of the respective leg-cuff, in which the free edge of the leg-cuff is contractible, by a distance of 10 mm or more, when the free edge of the leg-cuff is in a stretched state.

According to the above embodiment (2), it is assured that (b) the leg-cuffs can rise without being collapsed by the waist-cuff, and/or that (c) the ends of the respective leg-cuffs are interleaved between the waist-cuff and the chassis to prevent body waste from leaking through a clearance which would be otherwise defined between the leg-cuffs and the waist-cuff.

Furthermore, according to the embodiments in the above (ii) to (xviii), one or more advantageous effects set forth in (a)-(c), are better ensured, as well as one or more of the advantageous effects of the respective embodiments that have previously been referred to in the respective related descriptions are ensured.

The terms "first" and "second" herein are used merely for distinguishing between similar elements. Furthermore, the wording "first waist region" herein means one of the front and rear waist regions, and the wording "second waist region" herein means the other. Similarly, the wording "first end" of the leg cuff herein means one end of the longitudinally opposite ends which lying on the first waist region and the wording "second end" of the leg cuff herein means the other end lying on the second waist region.

The invention claimed is:

1. An absorbent article, comprising:
a chassis having longitudinal and transverse directions orthogonal to each other;
a skin-contact surface;
a first waist region;
a second waist region;
a crotch region extending in the longitudinal direction between said first waist region and said second waist region;
an absorbent structure;
a waist-opening defined by cooperation of said first and second waist regions;
a pair of leg-openings defined by cooperation of said first and second waist regions and said crotch region; and
a waist-cuff attached to said skin-contact surface in a region adjacent to said waist-opening in at least said first waist region of said first and second waist regions,
wherein
said waist-cuff is at least partially elastic,
said waist-cuff is left free from said chassis in a middle region overlapping said absorbent structure and in non-joined regions outboard of and in vicinities of transversely opposite lateral edges of said absorbent structure, said waist-cuff is directly joined to the skin-contact surface of said chassis in a joined region, the first and second waist regions are joined together at a plurality of bonding lines overlapping the joined region in a thickness direction of the chassis, and the joined region includes
  a first edge bonding region extending in transversely opposite side edges of the waist-cuff and in a waist-side end of the waist-cuff, and
  a second edge bonding region inward of the first edge bonding region in the longitudinal direction and in the transverse direction, the second edge bonding region extending along the non-joined regions and abutting an end of the absorbent structure.

2. The absorbent article defined by claim 1, further comprising:
  a pair of leg-cuffs attached to said skin-contact surface of said chassis, each of said leg-cuffs having
    a fixed edge attached to an associated one of said lateral edges of said absorbent structure,
    a free edge being elastically contractible in said longitudinal direction, and
    first and second ends respectively lying in said first and second waist regions,
  wherein at least said first end of said first and second ends is sandwiched between said chassis and said waist-cuff.

3. The absorbent article defined by claim 1,
  wherein said chassis comprises an inner sheet lying on a skin-contact side, and an outer sheet opposed to said inner sheet, and
  wherein said absorbent structure is sandwiched between said inner and outer sheets.

4. The absorbent article defined by claim 1,
  wherein said chassis comprises an inner sheet lying on a skin-contact side, and an outer sheet opposed to said inner sheet, and
  wherein said absorbent structure is provided on said inner sheet.

5. The absorbent article defined by claim 1,
  wherein said chassis comprises
    two waist members defining said first and second waist regions, respectively, and
    a crotch member defining said crotch region, and
  wherein said absorbent structure is provided on a skin-contact side of said crotch member.

6. The absorbent article defined by claim 1, wherein said waist-cuff is formed of an elastic fibrous non-woven fabric.

7. The absorbent article defined by claim 1, wherein said first and second waist regions are joined at the plurality of bonding lines along lateral edges thereof to define said waist-opening and said pair of leg-openings, with lateral edges of said waist-cuff being sandwiched between and bonded to said lateral edges of said first and second waist regions.

8. The absorbent article defined by claim 1, wherein said waist-cuff is configured to be spaced from said skin-contact surface toward a wearer's body under at least elastic contraction of said waist-cuff.

9. The absorbent article defined by claim 2, wherein said waist-cuff is configured to be spaced from said skin-contact surface toward the wearer's body under elastic contraction of said waist-cuff and said free edge of each of said leg-cuffs.

10. The absorbent article defined by claim 2, wherein said free edges of said leg-cuffs are located inboard of said fixed edges of said leg-cuffs.

11. The absorbent article defined by claim 1, wherein a width of each of said non-joined regions of said waist-cuff in the vicinities of the transversely opposite lateral edges of said absorbent structure is increased toward said crotch region.

12. The absorbent article defined by claim 1, wherein a width of each of said non-joined regions of said waist-cuff in the vicinities of the transversely opposite lateral edges of said absorbent structure is increased in a stepwise fashion toward said crotch region.

13. The absorbent article defined by claim 1, wherein a width of each of said non-joined regions of said waist-cuff in the vicinities of the transversely opposite lateral edges of said absorbent structure is gradually increased toward said crotch region.

14. The absorbent article defined by claim 1, wherein a width of each of said non-joined regions of said waist-cuff in the vicinities of the transversely opposite lateral edges of said absorbent structure is in a range of 10 to 30 mm.

15. The absorbent article defined by claim 1, wherein the waist-cuff is directly wholly joined to the skin-contact surface except in the non-joined regions and the middle region.

16. The absorbent article defined by claim 1, wherein
  the waist-cuff is directly joined to the skin-contact surface in the joined region and at least along transversely opposite side edges of the first waist region, and
  the joined region is adjacent to the waist-side end of the waist-cuff and adjacent to the non-joined regions.

17. The absorbent article defined by claim 1,
  wherein the waist-cuff comprises an elastic sheet and an inelastic sheet,
  wherein the inelastic sheet is provided only in a region of 5 mm or less from a crotch-side end of the waist-cuff.

18. The absorbent article defined by claim 2, wherein
  each of the non-joined regions of the waist-cuff extends in the longitudinal direction along a region of the respective leg-cuff, in which the free edge of the leg-cuff is contractible, by a distance of 10 mm or more, when the free edge of the leg-cuff is in a stretched state.

* * * * *